United States Patent [19]

Chang

[11] Patent Number: 4,736,046

[45] Date of Patent: Apr. 5, 1988

[54] β-ISOCYANATO ORGANOSILANES

[75] Inventor: Kuo Y. Chang, Midland, Mich.

[73] Assignee: The Dow Chemical Company, Midland, Mich.

[21] Appl. No.: 812,477

[22] Filed: Dec. 23, 1985

[51] Int. Cl.$^4$ .................................................. C07F 7/18
[52] U.S. Cl. ..................................... 556/414; 548/110
[58] Field of Search ......................................... 556/414

[56] References Cited

U.S. PATENT DOCUMENTS

| | | | |
|---|---|---|---|
| 3,113,146 | 12/1963 | Fielding et al. | 260/448.8 |
| 3,170,891 | 2/1965 | Speier | 260/37 |
| 3,178,391 | 4/1965 | Holtschmidt et al. | 260/45.5 |
| 3,511,866 | 5/1970 | Pepe | 260/448.2 |
| 3,584,024 | 6/1971 | Pepe | 260/448.2 N |
| 4,064,151 | 12/1977 | Hedaya et al. | 260/448.2 N |
| 4,115,539 | 9/1978 | Eisenhardt et al. | 424/1 |

OTHER PUBLICATIONS

Kricheldorf, Chemical Abstracts, vol. 79 (1973) 78669a.

Primary Examiner—Richard L. Raymond
Attorney, Agent, or Firm—Charles J. Enright

[57] ABSTRACT

Novel β-isocyanatoethoxy silanes and a method for their preparation is provided in which a 2-oxazolidinone is reacted with a halosilane to form a novel intermediate silyl-2-oxazolidinone product. The intermediate is then exposed to heat under reduced pressure to convert it to a β-isocyanatoethoxy silane. The difunctional monomeric products are useful as starting materials for a variety of silicone and polyurethane prepolymers and polymers.

3 Claims, No Drawings

β-ISOCYANATO ORGANOSILANES

BACKGROUND OF THE INVENTION

This invention relates to novel β-isocyanato silanes and methods for their synthesis, including methods for preparing novel oxazolidinone intermediate compounds.

Compounds containing isocyanate functional groups are widely used as crosslinking agents in various chemical reaction because of the extremely reactive nature of the isocyanate radical. For example, isocyanate compounds may be reacted with polyols to produce a wide variety of useful polyurethane compositions. Isocyanate compounds are also widely used to crosslink polyethers and polyesters in the manufacture of elastomers and resins. Where such isocyanate compounds also contain silane functional groups, they can be utilized to produce silicone polymeric products.

The commercial preparation of compounds containing an isocyanate functionality is carried out almost exclusively through the reaction of amines with phosgene gas. See, for example, Holtschmidt et al, U.S. Pat. No. 3,178,391, which uses a phosgenation reaction to produce silane-containing isocyanates and Pepe, U.S. Pat. No. 3,584,024, which also utilizes a phosgene reactant to produce isocyanato-substituted siloxanes.

However, the use of phosgene presents many manufacturing difficulties because of its toxicity and the handling problems it entails. Additionally, the reaction conditions utilized restrict, somewhat, the types of isocyanate compounds which may be produced.

Others have developed procedures for producing isocyanate compounds which avoid the use of phosgene as a reactant. For example, Speier, U.S. Pat. No. 3,170,891, teaches a method which involves reacting a silane with an acyl chloride and then decomposing the intermediate product to produce an isocyanato silane. Hedaya et al, U.S. Pat. No. 4,064,151, teach reacting amine starting materials with carbon dioxide in a triethylamine solvent to produce a carbamic acid salt. The carbamic acid salt is then reacted with a halosilane and the reaction product pyrolyzed to form a halosilyl isocyanate.

However, the need still exists in the art for a relatively simple procedure for producing isocyanato silanes which avoids the use of phosgene and which forms monomeric reactants which are useful in producing a wide range of polyurethane and silicone polymers.

SUMMARY OF THE INVENTION

The present invention avoids the use of phosgene as a reactant while providing novel difunctional monomeric reaction products which can be used for preparing a variety of prepolymers and polymers utilizing silicone and polyurethane chemistries. The novel difunctional monomers of the present invention have both an isocyanate functional group and either a vinyl or silicon hydride (Si—H) functional group. According to one aspect of the present invention, a process is provided for preparing the novel β-isocyanatoethoxy silanes which comprises reacting a 2-oxazolidinone having the formula

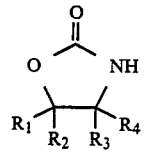

where $R_1$, $R_2$ $R_3$, and $R_4$ are hydrogen, alkyl, or aryl, with a halosilane of the formula

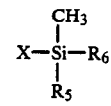

wherein $R_5$ is hydrogen, alkyl, or aryl; $R_6$ is hydrogen or a vinyl-containing alkyl, and X is a halogen. The reaction is preferably carried out in the presence of triethylamine in a solvent such as tetrahydrofuran.

The novel intermediate reaction product which is formed is a silyl-2-oxazolidinone having the formula

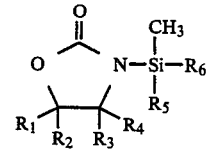

wherein $R_1$, $R_2$ $R_3$, $R_4$, $R_5$, and $R_6$ are as defined above. The silyl-2-oxazolidinone intermediate is then heated under reduced pressure to form a β-isocyanatoethoxy silane having the formula

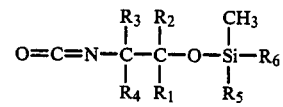

wherein $R_1$, $R_2$ $R_3$, $R_4$, $R_5$, and $R_6$ are as defined above.

Accordingly, it is an object of the present invention to provide novel β-isocyanato silanes and intermediate reaction products, and a process for their synthesis, which avoids the use of toxic phosgene as a reactant. This and other objects and advantages of the invention will become apparent from the following detailed description and the appended claims.

DETAILED DESCRIPTION OF THE PREFERRED EMBODIMENTS

In accordance with the process of synthesizing the novel products of the present invention, a 2-oxazolidinone is first reacted with a halosilane to form a silyl-2-oxazolidinone intermediate as shown below.

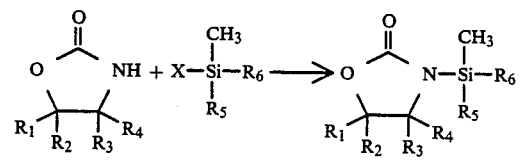

Functionality, $R_1$, $R_2$, $R_3$, $R_4$, and $R_5$ may be either hydrogen, an alkyl group such as methyl, ethyl, propyl, butyl, octyl, or the like, or an aryl group such as phenyl, benzyl, tolyl, and xylyl. The $R^6$ group may be either hydrogen, thus forming a silicon hydride functional group (Si—H), or an ethylenically unsaturated alkyl hydrocarbon functional group such as a vinyl group (—CH=CH$_2$) or a vinyl-containing group.

When $R_6$ is hydrogen, the silicon hydride functional group will undergo a hydrosilylation reaction with olefins and will also react with alcohols and silanols in the presence of a catalyst by eliminating hydrogen gas. Thus, it is expected that this monomer will be used in the preparation of block copolymers having properties of both polyurethanes and silicones and can be prepared from many readily avilable diols, amino alcohols, alkenols, biphenols, and hydroxyl-terminated polysiloxanes. The hydrogen gas produced may be used as a blowing agent in the manufacture of foams from those reactants. When $R_6$ is a vinyl or vinyl-containing group, the monomer resembles $\beta$-isocyanatomethacrylate and is expected to find similar applications in the production of polymeric resins.

The reaction is preferably carried out in a nonpolar solvent. Representative examples of suitable nonpolar solvents include hydrocarbons, halogenated hydrocarbons such as chloroform and methylene chloride, ethers, and nitriles. A preferrred solvent is tetrahydrofuran. Additionally, it is desirable that the reaction be carried out in the presence of a tertiary amine such as triethylamine, which acts as a scavenger for acids, such as hydrochloric acid, which may be formed.

The reaction is preferably carried out at or near the boiling point of the reactants, typically in the range of from about 130° to about 180° C. The use of distillation apparatus with provision for continuous reflux of the reaction mixture is also preferred.

Additionally, the pyrolysis reaction which converts the silyl-2-oxazolidinone intermediate to a $\beta$-isocyanato organosilane is preferably carried out under reduced pressure. Use of a reduced pressure in the range of about 0.5 to about 0.6 kg/cm$^2$, in conjunction with the elevated temperatures utilized, aids in avoiding undesirable side reactions during the procedure.

In order that the invention may be more readily understood, reference is made to the following examples, which are intended to illustrate the invention but are not to be taken as limiting the scope thereof.

EXAMPLE 1

A 3-dimethylsilyl-2-oxazolidinone was prepared in accordance with the following procedure. To a stirred mixture of 34.8 grams of 2-oxazolidinone and 40.4 grams of triethylamine in 600 ml of a tetrahydrofuran solvent, 45 ml of dimethylchlorosilane was added dropwise over a 30-minute period. The mixture was then heated in a distillation apparatus with continuous reflux for a period of 30 minutes. The resultant mixture was cooled and then filtered.

The filtrate was concentrated in a rotary evaporator to yield 54.8 grams of a brown liquid which was then distilled under reduced pressure to yield 31.2 grams of 3-dimethylsilyl-2-oxazolidinone.

EXAMPLE 2

A $\beta$-isocyanatoethoxydimethylsilane was prepared in accordance with the following procedure. 11.5 grams of the 3-dimethylsilyl-2oxazolidinone prepared in Example 1 was placed in a distillation apparatus and stirred and heated at a reduced pressure of 0.5 kg/cm$^2$. When the temperature reached 200° C. in the distillation pot, 5.42 grams of a liquid having a boiling point of about 130°–140° C. was distilled over. The liquid was identified using infrared and nuclear magnetic resonance techniques as $\beta$-isocyanato-ethoxydimethylsilane.

EXAMPLE 3

A 3-dimethylsilyl-5-methyl-2-oxazolidinone was prepared in accordance with the following procedure. A stirred mixture of 60.6 grams of 5-methyl-2-oxazolidinone and 62.4 grams of triethylamine was prepared in a tetrahydrofuran solvent. To this mixture, 67.5 ml of dimethylchlorosilane was added dropwise over a period of 90 minutes.

The mixture was then heated in a distillation apparatus with continuous reflux for 30 minutes. The mixture was cooled and then filtered. The filtrate was concentrated to yield 95 grams of a brown liquid. The brown liquid, which was determined to contain some unreacted 5-methyl-2-oxazolidinone, was further distilled at a reduced pressure of 0.001 k/cm$^2$ to yield 64.5 grams of 3-dimethylsilyl-5-methyl-2-oxazolidinone as identified utilizing nuclear magenetic resonance techniques.

EXAMPLE 4

A $\beta$-isocyanato-$\alpha$-methylethoxydimethylsilane was prepared in accordance with the following procedure. 14.7 grams of the 3-dimethylsilyl-5-methyl-2-oxazolidinone prepared in Example 3 was stirred and heated in a distillation apparatus at a reduced pressure of 0.5 kg/cm$^2$. During the next 90 minutes, approximately 7.9 grams of a liquid having a boiling point of between 145°–150° C. was distilled over. During this period, the pot temperature of the distillation apparatus increased from 213° to 260° C. The liquid was identified using nuclear magentic resonance techniques as $\beta$-isocyanato-$\alpha$-methylethoxydimethylsilane.

EXAMPLE 5

A 3-vinyldimethylsilyl-2-oxazolidinone was prepared in accordance with the following procedure. A mixture of 34.8 grams of 2-oxazolidinone and 48.17 grams of vinyldimethylchlorosilane was prepared in 750 ml of tetrahydrofuran solvent. 40.26 grams of triethylamine was added dropwise. The mixture was then heated in a distillation apparatus with continuous reflux for a period of 30 minutes.

The mixture was then cooled and filtered. The filtrate was concentrated to give 69.3 grams of a brown liquid. The brown liquid was then distilled under reduced pressure. A 31.0 gram fraction having a boiling point of between 130°–138° (at 0.008 kg/cm$^2$) was identified using nuclear magnetic resonance techniques to be 3-vinyldimethyl-silyl-2-oxazolidinone.

EXAMPLE 6

A $\beta$-isocyanatoethoxy-vinyldimethylsilane was prepared in accordance with the following procedure. Approximately 11.1 grams of the 3-vinyldimethylsilyl-2-oxazolidinone prepared in Example 5 was stirred and heated in a distillation apparatus. The pot temperature was maintained between 230°–250° C. by adjusting the pressure in the apparatus in the range of about 0.5 to about 0.6 kg/cm$^2$. 33.3 grams of a liquid having a boiling point of between 165°–175° at 0.51 kg/cm$^2$ was obtained. This liquid was redistilled to obtain substantially pure $\beta$-isocyanatoethoxy-vinyldimethylsilane as identified using nuclear magentic resonance techniques.

EXAMPLE 7

A 3-vinyldimethylsilyl-5-methyl-2-oxazolidinone was prepared in accordance with the following procedure. A stirred mxiture of 40.4 grams of 5-methyl-2-oxazolidinone and 45.45 grams of triethylamine in 750 ml of tetrahydrofuran was prepared. To this mixture, 50.64 grams of dimethylvinylchlorosilane was added dropwise at room temperature over a period of 90 minutes. The mixture was then heated in a distillation apparatus with continuous reflux for a period of 30 minutes.

The mixture was then cooled and filtered. The filtrate was concentrated in a rotary evaporator and the distilled under reduced pressure to yield 54.7 grams of a light yellow liquid which was found to have a boiling point of 84° C. at a pressure of 0.0007 kg/cm². The liquid was identified as 3-vinyldimethylsilyl-5-methyl-2-oxazolidinone using nuclear magnetic resonance techniques.

EXAMPLE 8

A β-isocyanato-α-methylethoxyvinyldimethylsilane was prepared in accordance with the following procedure. In a small distillation flask equipped with an addition funnel and a short column 40 milligrams of phenothiazine and 18.85 grams of the 3-vinyldimethylsilyl-5-methyl-2-oxazolidinone of Example 7 were mixed with stirring. The mixture was then heated to 240° C. under a reduced pressure of about 0.54 kg/cm².

11.9 grams of a liquid was distilled over at between 212°–230° C. The liquid was found to contain a 2:1 mixture of the starting material and product. The liquid was redistilled at a pressure of 0.029 kg/cm² to yield 3.51 grams of β-isocyanato-α-methyl-vinyldimethysilane as identified using infrared and nuclear magnetic resonance techniques.

Having described the invention in detail and by reference to preferred embodiments thereof, it will be apparent that modifications and variations are possible without departing from the scope of the invention defined in the appended claims.

What is claimed is:

1. A composition of matter of the formula

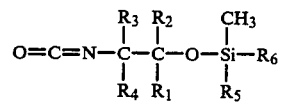

wherein $R_1$, $R_2$, $R_3$, $R_4$, and $R_5$ are hydrogen, alkyl, or aryl; and $R_6$ is hydrogen or an ethylenically unsaturated hydrocarbon functional group.

2. The composition of claim 1 wherein $R_6$ is hydrogen.

3. The composition of claim 1 wherein $R_6$ is a vinyl group.

* * * * *